(12) United States Patent
Deaciuc et al.

(10) Patent No.: US 8,084,501 B2
(45) Date of Patent: Dec. 27, 2011

(54) STABLE PROSTAGLANDIN-CONTAINING COMPOSITIONS

(75) Inventors: Victor Deaciuc, San Diego, CA (US); Michael Hagan, La Mesa, CA (US); Hashem Heiati, San Diego, CA (US); Karen K. Jette, San Diego, CA (US); Gary C. Visor, San Diego, CA (US); Ian G. C. McAffer, Kent (GB); Peter Tasko, Hertfordshire (GB)

(73) Assignees: Breath Limited, Kent (GB); Resolution Chemicals Limited, Hertfordshire (GB)

( * ) Notice: Subject to any disclaimer, the term of this patent is extended or adjusted under 35 U.S.C. 154(b) by 190 days.

(21) Appl. No.: 11/336,115

(22) Filed: Jan. 20, 2006

(65) Prior Publication Data

US 2006/0270735 A1   Nov. 30, 2006

(30) Foreign Application Priority Data

Jan. 20, 2005   (GB) .................................. 0501192.9

(51) Int. Cl.
*A61K 31/19* (2006.01)
*A61K 31/5575* (2006.01)

(52) U.S. Cl. ..................................... 514/573; 424/78.04

(58) Field of Classification Search .......................... None
See application file for complete search history.

(56) References Cited

U.S. PATENT DOCUMENTS

| | | | |
|---|---|---|---|
| 1,366,215 A | 1/1921 | Ruths | |
| 5,165,918 A * | 11/1992 | Heyl et al. | 424/78.04 |
| 5,631,287 A | 5/1997 | Schneider | |
| 5,670,537 A | 9/1997 | Canetta et al. | |
| 5,849,792 A | 12/1998 | Schneider | |
| 5,889,052 A | 3/1999 | Klimko et al. | |
| 5,972,991 A | 10/1999 | Burk | |
| 6,011,062 A | 1/2000 | Schneider et al. | |
| 6,235,781 B1 | 5/2001 | Weiner et al. | |
| 6,319,943 B1 | 11/2001 | Joshi et al. | |
| 6,417,228 B1 | 7/2002 | Klimko | |
| 6,743,439 B1 * | 6/2004 | Castillo et al. | 424/427 |
| 2002/0103255 A1 | 8/2002 | Hellberg et al. | |
| 2003/0147823 A1 | 8/2003 | Woodward et al. | |
| 2004/0023954 A1 * | 2/2004 | Ling et al. | 514/228.2 |
| 2004/0076678 A1 | 4/2004 | Ueno | |
| 2004/0082660 A1 | 4/2004 | Ueno | |
| 2004/0097592 A1 | 5/2004 | Morishima et al. | |

FOREIGN PATENT DOCUMENTS

| | | | |
|---|---|---|---|
| AU | 704670 | | 10/1998 |
| EP | 0603800 A1 * | | 6/1994 |
| EP | 1 321 144 | | 6/2003 |
| WO | WO-95/18102 | | 7/1995 |
| WO | WO 98/41208 | * | 9/1998 |
| WO | WO-99/02164 | | 1/1999 |
| WO | WO-99/02165 | | 1/1999 |
| WO | WO-99/12899 | | 3/1999 |
| WO | WO-00/20386 | | 4/2000 |
| WO | WO-00/40248 | | 7/2000 |
| WO | WO-02/38158 | | 5/2002 |
| WO | WO-2004/022063 | | 3/2004 |

OTHER PUBLICATIONS

Product page for Sigma T6687 from www.sigmaldrich.com, accessed Dec. 4, 2007.*
Alexander et al., Annals of Pharmacotherpay, 36(3), p. 504-511, 2002.*
BASF Technical Leaflet, "Cremophor EL", pp:1-7, Jul. 1997.
Kerstetter el al., "Prostaglandin F2 Alpha-1-Isopropylester Lowers Intraocular Pressure Without Decreasing Aqueous Humor Flow", *J. Ophthalmol*, 105:30-34 (1988). (abstract).
Oda et al., Cell Injury Effect of Isopropyl Unoprostone, an Antiglaucoma Agent, on Cultured Human Conjunctival Cells, *J. Ocul Pharmacol Ther.*, 15:489-496 (1999). (abstract).
Tabassi et al., The Effects of Polysorbate Surfactants on the Structure of Mucus Glycoproteins, http://diglib.tums.ac.ir/U.j/daru/vol9n12/sajjadi.htm, pp:1-10 (2004).
Ciucanu et al., "Derivatizations of prostaglandins and related compounds to (methoxime) alkyl ester alkyl ether derivatives for gas chromatographic analysis," *Chemical Abstracts*, 109:664 (1988).
Ikegami et al., "9,15-Bis(arylsilyl)prostaglandin $F_2\alpha$ derivatives," *Chemical Abstracts*, 105:650 (1986).
Lijebris et al., "Ligand-controlled palladium-catalyzed intramolecular reactions of phenyl-substituted prostaglandin $F_2\alpha$ analogues," *Tetrahedron*, 51:9139-9154 (1995).
Miyazaki et al., "Dimethylisopropylsilyl ether derivatives in gas chromatography mass spectrometry fo prostaglandins and thromboxane B2," *Chemical Abstracts*, 96:90-91 (1982).
Morozowich et al., "Prostaglandin prodrugs. II: New method for synthesizing prostaglandin C1-aliphatic esters," *Chemical Abstracts*, 91:603 (1979).
Waddell et al., "Combined capillary column gas chromatography negative ion chemical ionization mass spectrometry of prostanoids," *Chemical Abstracts*, 99:87498 (1983).
European Search Report for corresponding Application No. 06178670.0, dated Mar. 18, 2008.
United Kingdom Intellectual Property Office Search Report for corresponding Application No. GB0501192.9, dated Apr. 19, 2005.
International Search Report for corresponding International Application No. PCT/US2006/001626, dated Jul. 25, 2006.
Written Opinion of the International Searching Authority for corresponding International Application No. PCT/US2006/001626, dated Jul. 25, 2006.
International Preliminary Report on Patentability for corresponding International Application No. PCT/US2006/001626, dated Jul. 24, 2007.

* cited by examiner

*Primary Examiner* — Nissa Westerberg
(74) *Attorney, Agent, or Firm* — Marshall, Gerstein & Borun LLP

(57) ABSTRACT

A pharmaceutical composition containing a prostaglandin and an alkanoic acid ester of a polyethoxylated sorbitol in an amount effective to enhance the chemical stability of the prostaglandin, and the use thereof for treating ophthalmic conditions. Also disclosed are methods for enhancing the chemical stability of a prostaglandin-containing composition by using an alkanoic acid ester of a polyethoxylated sorbitol.

7 Claims, No Drawings

STABLE PROSTAGLANDIN-CONTAINING COMPOSITIONS

CROSS-REFERENCE TO RELATED APPLICATION

Not Applicable.

FEDERALLY SPONSORED RESEARCH OR DEVELOPMENT

Not Applicable.

TECHNICAL FIELD

This invention relates to prostaglandin-containing compositions. In particular, to stable prostaglandin-containing compositions that can be used in pharmaceutical compositions and medicaments for the treatment of ophthalmic conditions, and methods for producing the same.

BACKGROUND OF THE INVENTION

A common ophthalmic condition is ocular hypertension. This term is used to describe the condition wherein the pressure inside the eye is higher than the normal range. Elevated intraocular pressure may occur, for example, due to (i) excessive aqueous fluid production, or (ii) blocking of the passages that normally allow fluid in to drain from the eyes. Generally with this condition there are no detectable changes in vision or damage to the structure of the eyes. The term "ocular hypertension" is also used to distinguish from the more serious eye condition, glaucoma.

Prolonged or severe ocular hypertension can sometimes lead to glaucoma, which causes damage to the optic nerve and loss of vision. Glaucoma is, in fact, one of the leading causes of blindness. The illness is most prevalent in people over the age of 40, particularly those who have a family history of glaucoma, and especially those who are very nearsighted or diabetic.

Although ocular hypertension and glaucoma cannot be cured, these conditions can be treated to reduce the risk of damage to the eye. The treatment regime usually begins with prescription eye drops and/or medicines to lower intraocular pressure. A number of alternative prescription eye drops are available, which contain different active ingredients and reduce the pressure in the eye by different mechanisms. For instance, the medicament may reduce the production of aqueous humour, or may increase the rate of fluid drainage from the eye.

Prostaglandin analogues are a common active ingredient of eye drops. They work by increasing the rate of fluid outflow from the anterior chamber of the eye. However, prostaglandins have a very low solubility in water and are generally also quite unstable. Therefore, in order to produce a commercially viable eye drop, the prostaglandin analogue must be both solubilised and stabilised so that the level of active ingredient remains constant over the lifetime of the medicament.

Poor solubility in water is not uncommon amongst commercially useful drugs. In fact, increasing the bioavailability of poorly soluble drug compounds is one of the greatest challenges the pharmaceutical industry faces. Cyclodextrins have been used as solubilisers and stabilisers of prostaglandins (EP 435 682 A2) and many other drugs (for a review, see Loftsson T. & Brewster M. E. Pharmaceutical applications of cyclodextrins. 1. Drug solubilization and stabilization, *J. Pharm. Sci.*, 1996, 85(10), 1017-25). Also, a wide variety of surfactants, cosolvents and solubilisers have been developed to increase the water-solubility of drugs (see Samuel H. Yalkowski, Solubility and Solubilization in Aqueous Media, *Am. Chem. Soc.* 1999). However, the relative success of each of these approaches is variable and critically dependent on the particular drug and solvent system selected.

For instance, surfactants can be cationic, anionic, amphoteric and non-ionic, and whereas certain surfactants may be simply ineffective, others may actually enhance the chemical breakdown of a particular drug. Non-ionic surfactants such as polyethoxylated castor oils have been widely used as solubilisers, for instance, of the antibiotic Cyclosporin A (Ran Y. et al., Solubilization of Cyclosporin A. *AAPS Pharm Sci Tech.*, 2001, 2(1), article 2), and as stabilising agents, such as for vitamin preparations (U.S. Pat. No. 4,075,333).

Polyethoxylated castor oils have also been used to create stable solutions for use in ophthalmic formulations containing, for example; ortho-(2,6-dichlorophenyl)-amino-phenylacetic acid for the control of eye inflammation (U.S. Pat. No. 4,960,799), vitamin A for the treatment of dry-eye syndrome (U.S. Pat. No. 5,185,372), and prostaglandin compositions for treating ocular hypertension and glaucoma (U.S. Pat. No. 5,631,287).

The solution stability of prostaglandins has been compared in both U.S. Pat. No. 5,631,287 and U.S. Pat. No. 5,849,792. In these studies it was shown that the use of polyethoxylated castor oils enhanced the stability of prostaglandins in ophthalmic formulations. In comparison, it was demonstrated that an alternative non-ionic surfactant, polysorbate 80, was unsuitable for use in a storage-stable solution. Particularly preferred polyethoxylated castor oils were Cremophor® EL and Alkamuls® EL-620, which were found to be far superior to polysorbate 80. However, polyethoxylated castor oils may not be tolerated by certain patients and accordingly, it has become imperative to find other stabilising and solubilising agents.

It has now been surprisingly found, however, that using carefully selected proportions, polysorbates are effective at stabilising prostaglandin solutions, and can provide enhanced levels of stability and freedom from impurities (such as breakdown products) in the final formulation, compared to use of polyethoxylated castor oils. The compositions of the invention therefore provide an important alternative to the use of formulations containing polyethoxylated castor oils, such as for use in ophthalmic medicaments, particularly for individuals whom are sensitive to the currently available prescription medications.

DETAILED DESCRIPTION OF THE INVENTION

According to the invention there is provided a pharmaceutical composition comprising a prostaglandin of formula (I):

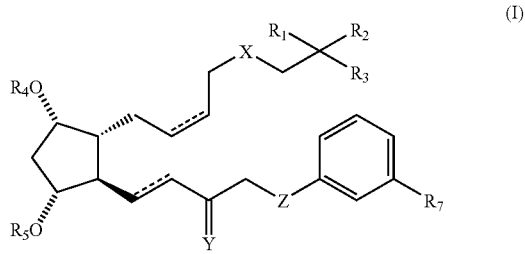

or a pharmaceutically acceptable salt or ester thereof, wherein:

$R_1$ is selected from H, $C_1$-$C_6$ alkyl, $C_5$-$C_{10}$ aryl, $C_3$-$C_8$ cycloalkyl, —$OR_8$, —$C(O)R_8$, —$C(O)_2R_8$, —$N(R_8)_2$, —$C(O)N(R_8)_2$, and a cationic salt moiety;

$R_2$ and $R_3$ may be the same or different and are each independently selected from H, and $C_1$-$C_6$ alkyl; or $R_2$ and $R_3$ taken together may represent O;

X is selected from O, S, and $CH_2$;

- - - - represents any combination of a single bond, or a cis or trans double bond for the alpha chain (upper); and a single bond or a trans double bond for the omega (lower) chain;

$R_4$ and $R_5$ may be the same or different and are each independently selected from H, $C_1$-$C_6$ alkyl, $C_5$-$C_{10}$ aryl, $C_3$-$C_8$ cycloalkyl, and —C(O)$R_8$;

Y is O or H and $OR_6$ in either R or S configuration wherein:

$R_6$ is selected from H, $C_1$-$C_6$ alkyl, and —C(O)$R_8$;

Z is selected from O and $CH_2$;

$R_7$ is selected from H, Cl and $CF_3$; and $R_8$ is selected from H and $C_1$-$C_6$ alkyl;

an alkanoic acid ester of a polyethoxylated sorbitol in an amount effective to enhance chemical stability of the prostaglandin or pharmaceutically acceptable salt or ester thereof; and a pharmaceutically acceptable carrier.

Preferred compositions contain prostaglandin at a concentration of 0.0001% to 0.1% w/v, more preferably at a concentration of 0.0005% to 0.025% w/v, still more preferably at a concentration of 0.001% to 0.005%, and most preferably the prostaglandin is at a concentration of 0.004% w/v.

The alkanoic acid ester of a polyethoxylated sorbitol is preferably present at a concentration of 0.1% to 3.0% w/v; more preferably at a concentration of 0.2% to 1.0% w/v; still more preferably at a concentration of 0.3% to 0.7% w/v; and most preferably at a concentration of about 0.5% w/v.

In preferred compositions of the invention, the alkanoic acid of the alkanoic acid ester of a polyethoxylated sorbitol is selected from the group consisting of monolaurate, monopalmitate, monostearate, monooleate and monoisostearate. The most preferred alkanoic acid ester of a polyethoxylated sorbitol is polysorbate 80, wherein the alkanoic acid ester of a polyethoxylated sorbitol is monooleate.

The compositions of the invention are preferably those of formula (I), wherein: $R_1$ is —$OR_8$ or —$N(R_8)_2$; and $R_2$ and $R_3$ taken together represent O. More preferably, those wherein: $R_1$ is —$OCH(CH_3)_2$ or —$NHC_2H_5$; $R_2$ and $R_3$ taken together represent O; X is $CH_2$; $R_4$ and $R_5$ are each H; Y is $OR_6$, wherein $R_6$ is H; Z is O or $CH_2$; and $R_7$ is H or $CF_3$.

Still more preferred prostaglandins include: travoprost [formula (II)]; latanoprost [formula (III)]; and bimatoprost [formula (IV)];

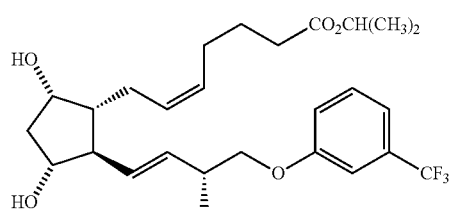

(II)

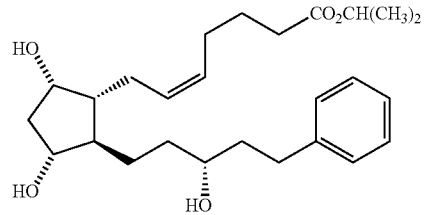

(III)

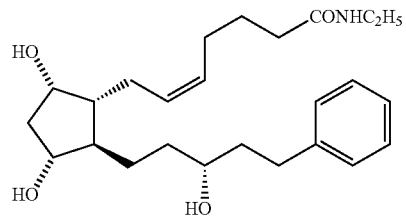

(IV)

Most preferably, the prostaglandin is travoprost [(Z)-7-[(1R,2R,3R,5S)-3,5-dihydroxy-2-[1E,3R)-3-hydroxy-4-[(α,α,α-trifluoro-m-tolyl)oxy]-1-butenyl]cyclopentyl]-5-heptenoate] of formula (II).

Accordingly, a preferred composition of the invention comprises: travoprost 0.002-0.008% w/v; polysorbate 80 0.4-0.6% w/v; benzalkonium chloride 0.010-0.020% w/v; EDTA 0.05-0.2% w/v; boric acid 0.1-0.4% w/v; tromethamine 0.08-0.2% w/v; and mannitol 2.0-8.0% w/v.

Compositions according to the invention are preferably formulated so as to be suitable for topical applications, such as in the form of an ophthalmic solution. Such compositions are preferably suitable for use in the treatment of ophthalmic conditions, such as glaucoma and/or ocular hypertension.

Thus, use of the compositions of the invention in the manufacture of a medicament for the treatment of ophthalmic conditions in a mammal is also envisaged. Most preferably the ophthalmic conditions are glaucoma and/or ocular hypertension and the mammal is a human.

In accordance with the invention there is also provided a method of enhancing the chemical stability of a composition comprising a prostaglandin or a pharmaceutically acceptable salt or ester thereof, wherein the method comprises adding an effective amount of an alkanoic acid ester of a polyethoxylated sorbitol to the composition.

In a preferred method of the invention, the alkanoic acid ester of a polyethoxylated sorbitol is present at a concentration of 0.1% to 3.0% w/v; more preferably at a concentration of 0.2% to 1.0% w/v; still more preferably at a concentration of 0.3% to 0.7% w/v; and most preferably at a concentration of about 0.5% w/v.

More preferred methods of the invention are those wherein the alkanoic acid of the alkanoic acid ester of a polyethoxylated sorbitol is selected from the group consisting of monolaurate, monopalmitate, monostearate, monooleate and monoisostearate. The most preferred alkanoic acid ester of a polyethoxylated sorbitol is polysorbate 80, wherein the alkanoic acid ester of a polyethoxylated sorbitol is monooleate.

The methods of the invention are especially useful for enhancing the chemical stability of compositions comprising a prostaglandin of the formula (I), as defined in any of the above embodiments. Accordingly, most preferably in the method of the invention the prostaglandin is travoprost of formula (II) above.

The compositions described herein contain at least one prostaglandin. The term "prostaglandin" relates to the class of naturally occurring prostaglandins and to derivatives and analogues thereof, either natural or synthetic. Also comprised within the term are pharmaceutically acceptable derivatives and salts of such prostaglandins.

Prostaglandins are a diverse family of hormone-like molecules derived from prostanoic acid:

Prostanoic acid

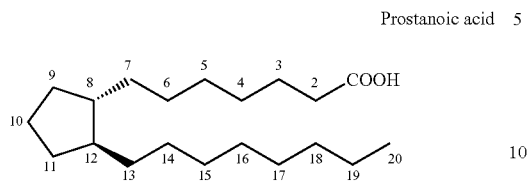

The prostaglandin family is further subdivided according to the structure of the five membered ring, such that there are the A-series (PGA), B-series (PGB), C-series (PGC), D-series (PGD), E-Series (PGE) F-series (PGF) and J-series (PGJ) of prostaglandins. In addition, prostaglandin nomenclature reflects the number of unsaturated carbon-carbon bonds in the side chains. Thus, a molecule having two double bonds is given the subscript "2", e.g. $PGA_2$. Travoprost [see formula (II)] is member of the $PGF_2$ class of prostaglandins.

Analogues and derivatives of known prostaglandins include, without limitation, modifications to the alkyl side chains, such as alkyl substitutions (e.g. methyl, dimethyl, ethyl etc.) and the level of saturation or unsaturation of the side chains. Derivatives and analogues may also contain modified groups such as (substituted) phenyl, phenoxy etc. as depicted in formula (II). Synthetic or natural analogues and derivatives of prostaglandins have physiological properties that are generally similar to those of natural prostaglandins. However, such analogues and derivatives may exhibit properties that are enhanced or otherwise modified in a particular aspect, for instance, improved physiological activity or increased chemical stability.

Pharmaceutically acceptable salt and ester derivatives may be modified at any suitable position, such as at the oxygen atom of an available hydroxyl or carboxyl group.

As used herein the term:

"alkyl" means a straight or branched carbon chain having from 1-20 carbon atoms, preferably from 1-12 carbon atoms and more preferably from 1-6 carbon atoms;

"cycloalkyl" represents a saturated carbocyclic ring or rings having from 3-20 carbon atoms, preferably from 3-10 carbon atoms, and more preferably from 3-8 carbon atoms; said cycloalkyl ring being unsubstituted or optionally substituted with one or more substituents (e.g. 1, 2 or 3) selected from; $C_1$-$C_6$ alkyl, halo, haloalkyl, hydroxyl and amino;

"aryl" means a carbocyclic group containing from 5-15 carbon atoms and having at least one (e.g. 1, 2 or 3) aromatic rings. Typical aryl moieties include phenyl and napthyl. Said aryl group being unsubstituted or optionally substituted with one or more substituents (e.g. 1, 2 or 3) selected from; $C_1$-$C_6$ alkyl, halo, haloalkyl, hydroxyl and amino, and with all available substitutable carbon atoms of the carbocyclic group being intended as possible points of attachment;

"halo" represents fluoro, chloro, bromo and iodo; and is most preferably chloro;

"haloalkyl" is a alkyl group as defined above, which is substituted with one or more halo groups (e.g. 1, 2 or 3), preferably the alkyl group is a $C_1$-$C_6$ alkyl group, and more preferably the haloalkyl is $CF_3$.

In more preferred embodiments of the invention, the prostaglandin is selected from: travoprost [formula (II)]; latanoprost [formula (III)]; and bimatoprost [formula (IV)];

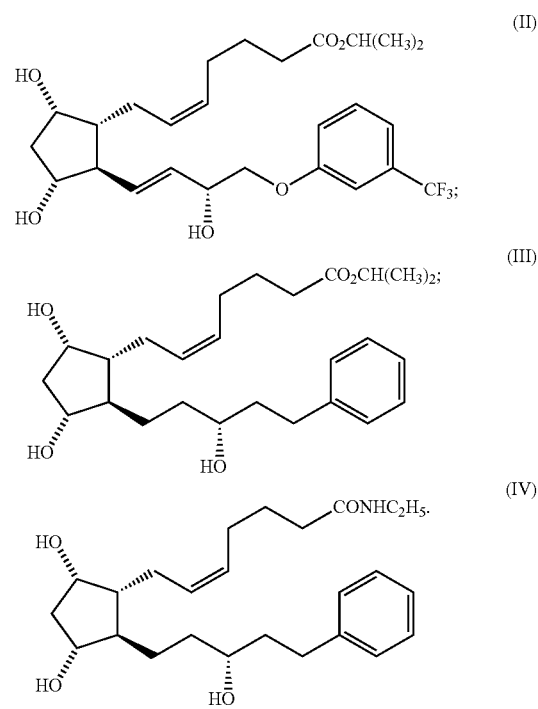

Most preferably, however, the prostaglandin is isopropyl (Z)-7-[(1R,2R,3R,5S)-3,5-dihydroxy-2-[1E,3R)-3-hydroxy-4-[(α,α,α-trifluoro-m-tolyl)oxy]-1-butenyl]cyclopentyl]-5-heptenoate (i.e. travaprost), of formula (II).

The compositions of the invention may contain any concentration of prostaglandin that is suitable for the intended use. Thus, a wide range of dose forms of the compositions of the invention is envisaged. However, preferred compositions contain prostaglandin at a concentration of 0.0001% to 0.1% w/v; more preferably at a concentration of 0.0005% to 0.025% w/v; still more preferably at a concentration of 0.001% to 0.005% w/v; and most preferably the prostaglandin is at a concentration of 0.004% w/v.

An alkanoic acid ester of a polyethoxylated sorbitol is commonly referred to as a "polysorbate". Polysorbates are a class of non-ionic, hydrophilic surfactants, which are generally soluble or dispersible in water and soluble to varying degrees in organic solvents. Accordingly, polysorbates are used for producing oil-in-water emulsifications, dispersions or solutions of oils or other water-insoluble material.

Polysorbates are formed by reacting polyoxyethylene sorbitol with an alkanoic acid to give an ester having the structure of formula (V):

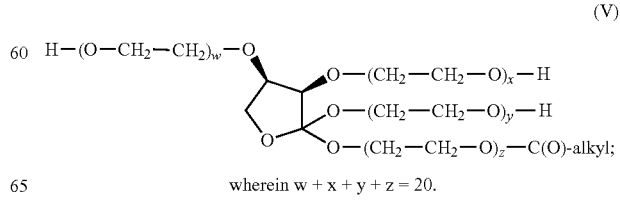

wherein w + x + y + z = 20.

The resultant polysorbate is named according to the alkanoate group that derives from the alkanoic acid [see bold portion in formula (V)]. Thus, a large range of polysorbates are known, including those having a monolaurate moiety (polysorbate 20), a monopalmitate moiety (polysorbate 40), a monostearate moiety (polysorbate 60), a monooleate moiety (polysorbate 80), a trioleate moiety (polysorbate 85) and an monoisostearate moiety (polysorbate 120). Furthermore, polysorbates that do not contain 20 oxyethylene groups are known (i.e. $w+x+y+z \neq 20$). Such polysorbates include polysorbate 21, polysorbate 61 and polysorbate 81.

The compositions of the invention generally contain at least one polysorbate, such as one of those listed above. Preferred polysorbates include polysorbate 20, 40, 60, 80 and 120; with polysorbate 80 being the most preferred.

The concentration of polysorbate that is required to enhance the chemical stability of the prostaglandin will depend on the exact proportions of other ingredients, such as, for example, the amount of prostaglandin in the composition. However, typical compositions contain at least one polysorbate at a concentration of 0.1% to 3.0% w/v; more preferably at a concentration of 0.2% to 1.0% w/v; still more preferably at a concentration of 0.3% to 0.7% w/v; and most preferably at a concentration of about 0.5% w/v.

In addition to the above-described ingredients, the compositions of the invention may contain any further components that are useful in the required formulations, for example, to produce a formulation that is suitable for topical ophthalmic applications; such as solutions, lotions, emulsions, suspensions and gels. Accordingly, suitable additional ingredients include, without limitation, antioxidants, antimicrobial preservatives, buffers, tonicity/osmolarity agents etc. Compositions may also include additional active ingredients such as anti-inflammatory agents.

Antioxidants help to extend the shelf-life of a product by reducing the oxidation rate of the active ingredient or excipient. Products that are kept in direct sunlight are particularly at risk of oxidation. Examples of antioxidants include butylated hydroxytoluene (BHT), ascorbic acid, sodium bisulphite and sodium salts of edetate (EDTA). Other suitable antioxidants are known to the person of skill in the art. The concentration of antioxidant or antimicrobial preservative necessary may depend on the choice of preservative, the intended use and the desired shelf-life of the composition. The required concentration can be readily determined by the skilled person, but is generally in the range 0.001% to 1% w/v. In a preferred composition the amount of antimicrobial preservative is in the range of 0.01 to 0.02% w/v and the amount of antioxidant is in the range 0.05% to 0.2% w/v.

Antimicrobial preservatives are used to prevent or inhibit the growth of microorganisms that could present a risk of infection. These are particularly important in compositions including water and which are used repeatedly, such as eye drops. Antimicrobial preservatives may be used in any effective amount. Typical antimicrobial preservatives are well known to the person of skill in the art and include, without limitation, benzalkonium chloride, chlorobutanol, Polyquad® and parabens, such as methyl or propyl paraben.

Tonicity and osmolarity agents include common salts, for example, sodium chloride and potassium chloride, and also compounds such as sucrose, mannitol, dextrose, glycerine and propylene glycol. However, other suitable tonicity and osmolarity agents known to the person of skill in the art may also be used. The concentration of tonicity and osmolarity agents can of course vary, and may be for instance in the range 0.5% to 10% w/v. Typically, however, for ophthalmic applications the tonicity of the composition may be adjusted to approximate the osmotic pressure of normal ophthalmic fluids and may also be isotonic with physiological saline. A preferred composition of the invention contains approximately 4.6% w/v mannitol.

Buffers are important for maintaining the pH of a formulation at a level appropriate for the intended use, for instance, so as not to cause discomfort or damage to the region to which the composition is applied. The compositions of the invention are preferably maintained at a pH in the range of 5.0 to 7.5, preferably in the range of 6.0 to 7.0 and most preferably the compositions are at a pH of approximately 6.0. Any suitable buffer that is capable of maintaining the pH of the composition within the above range (i.e. between pH 5.0 and pH 7.5) may be used. By way of example, suitable buffering agents include, but are not limited to; tromethamine, acetic acid, boric acid, citric acid, TRIS, HEPES, MOPS, sodium bicarbonate and phosphate buffers. When used, buffers will generally be in amounts ranging from 0.02 to 0.2% w/v, preferably 0.08 to 0.2% w/v and more preferably at 0.1 to 0.15% w/v. However, the exact quantity used may depend on the type of buffer used, the desired pH and the proportions of additional ingredients in the composition. For example, in a preferred formulation of the invention, tromethamine is used at a level of 0.12% w/v and the pH of the composition is approximately 6.0.

Compositions according to the invention may also include viscosity builders or demulcents, such as polyvinylpyrrolidone (PVP), cellulose derivatives, glycerin, and the like. If used, such viscosity builders or demulcents may be employed in a total amount ranging from about 0.01% to about 5.0% w/v. The viscosity of the final formulation is adjusted to any suitable level; for example, the viscosity may be in the range of 10 cps to 50 cps.

In general, aqueous ophthalmic solutions used in accordance with this invention may be formulated, for example, in accordance with the procedures set forth in Chapter 83 of Remington's Pharmaceutical Sciences, 14th Edition, Mack Publishing Company.

The compositions described herein may be used in the treatment of ophthalmic conditions, particularly conditions such as glaucoma and ocular hypertension. Furthermore, the compositions described can be combined with any additional pharmaceutically acceptable carriers or adjuvants as may be necessary, and incorporated into medicaments. Such procedures and ingredients are known to the person of skill in the art. Accordingly, the invention provides for the use of compositions of the invention in the manufacture of a medicament for treating ophthalmic conditions, particularly in a mammal, and preferably in a human patient. Such medicaments are particularly useful in the treatment of glaucoma and ocular hypertension.

The invention also provides a method of enhancing the chemical stability of a composition comprising a prostaglandin or a pharmaceutically acceptable salt or ester thereof. In the method of the invention an alkanoic acid ester of a polyethoxylated sorbitol (a polysorbate) is added to a composition containing a prostaglandin in an amount effective to enhance the chemical stability of the prostaglandin. Such a composition may comprise one or more prostaglandins selected from the group of natural PGA, PGB, PGC, PGD, PGE, PGF or PGJ prostaglandins; or may be selected from natural or synthetic derivatives or analogues thereof. Particularly preferred prostaglandins include the PGF series of prostaglandins as well as analogues and derivatives thereof. For example, preferred prostaglandins include: travoprost, latanoprost and bimatoprost; with the most preferred prostaglandin derivative being (Z)-7-[(1R,2R,3R,5S)-3,5-dihydroxy-2-[1E,3R)-3-hydroxy-4-[(α,α,α-trifluoro-m-tolyl)oxy]-1-butenyl]cyclopentyl]-5-heptenoate (i.e. travoprost) of formula (II).

The invention will now be further illustrated by the following Examples.

EXAMPLES

Example 1

To assay the chemical stabilising effect of polysorbates on prostaglandin-containing compositions, a comparative study was carried out.

Six different formulations (F1 to F6) were produced according to the formulations given in the table below (Table 1). In all cases the formulations were made by first dissolving the travoprost in a mixture of water, benzalkonium chloride (BAK) and surfactant (e.g. polysorbate 80, tyloxapol and cremaphor RH40). Finally, the remaining components were added to the resultant solution containing travoprost. Placebos were prepared of all formulations without the addition of prostaglandin.

The compositions (F1 to F6) were then incubated at a range of constant temperatures of 5° C., 25° C., 40° C., 55° C. and 75° C., and assayed for activity/potency and proportion of impurities, at time points of 0, 1, 3, 7, 14 and 21 days (see Tables 2 and 3).

The relative potency/activity of the travoprost formulations were tested at each of the time points noted above and the results, normalised relative to the starting activity, are shown in Table 2.

These results show that the composition of F2, which contained polysorbate 80 as the surfactant had very similar chemical stability to the commercially available formulation (F6) and the in-house composition made according to the specification of the commercially available product (F4). In fact, after 21 days at a temperature of 75° C. the composition containing the polysorbate (F2) actually displayed a greater activity/potency (97%), relative to the commercial product (F6, activity/potency 42%). Also after 21 days at 75° C., the commercial formulation that had been spiked with 0.4% w/v ethanol (F5) demonstrated greater activity/potency (97%) than the commercial product itself (F6, activity/potency 42%).

The extent of chemical breakdown of the prostaglandin component (travoprost) in each composition was calculated using HPLC analysis to measure the proportion of the primary degradant free acid compound. The result of this analysis, expressed as an average of five samples, is shown in Table 3.

The results show that the composition containing polysorbate 80 as the surfactant and stabiliser (F2) is less susceptible to chemical degradation at 55° C. and 75° C. than the commercially available preparation, which contains a polyethoxylated castor oil (i.e. chremophor) as the surfactant and stabiliser (F6). The commercially available composition that had been spiked with 0.4% w/v ethanol (F5) also appears to be more chemically stable than the commercial preparation (F6).

TABLE 1

Travoprost formulations used in assays of Example 1.

| Component | F1 % w/v | F2 % w/v | F3 % w/v | F4* % w/v | F5* % w/v | F6* % w/v |
|---|---|---|---|---|---|---|
| Travoprost | 0.004 | 0.004 | 0.004 | 0.004 | 0.004 | 0.004 |
| BAK | 0.1 | 0.015 | 0.015 | 0.015 | 0.015 | 0.015 |
| polysorbate 80 | — | 0.5 | — | — | — | — |
| tyloxapol | — | — | 0.5 | — | — | — |
| cremaphor RH40 | — | — | — | 0.5 | 0.5 | 0.5 |
| EDTA | 0.1 | 0.1 | 0.1 | 0.1 | 0.1 | 0.1 |
| boric acid | 0.3 | 0.3 | 0.3 | 0.3 | 0.3 | 0.3 |
| tromethamine | 0.12 | 0.12 | 0.12 | 0.12 | 0.12 | 0.12 |
| mannitol | 4.6 | 4.6 | 4.6 | 4.6 | 4.6 | 4.6 |
| ethanol | — | — | — | — | 0.4 | — |

BAK = benzalkonium chloride
*F4 is a composition made according to a commercially available formulation, Travatan ®;
*F5 is a commercially available formulation, Travatan ®, which has been spiked with ethanol;
*F6 is a commercially available formulation, Travatan ®.

TABLE 2

Relative potency of travoprost (%) normalised against time zero (0).

| Temp. (° C.) | Time (days) | F1 | F2 | F3 | F4 | F5 | F6 |
|---|---|---|---|---|---|---|---|
| 5 | 0 | 100 | 100 | 100 | 100 | 100 | 100 |
|   | 1 | 101 | 101 | 101 | 100 | 100 | 101 |
|   | 3 | 100 | 100 | 100 | 100 | 101 | 99 |
|   | 7 | 100 | 103 | 99 | 99 | 100 | 100 |
|   | 14 | ND | ND | ND | ND | ND | ND |
|   | 21 | ND | ND | ND | ND | ND | ND |
| 25 | 0 | 100 | 100 | 100 | 100 | 100 | 100 |
|   | 1 | ND | ND | ND | ND | ND | ND |
|   | 3 | 101 | 100 | 100 | 101 | 100 | 100 |
|   | 7 | 103 | 100 | 99 | 99 | 99 | 99 |
|   | 14 | ND | ND | ND | ND | ND | ND |
|   | 21 | ND | ND | ND | ND | ND | ND |
| 40 | 0 | 100 | 100 | 100 | 100 | 100 | 100 |
|   | 1 | ND | ND | ND | ND | ND | ND |
|   | 3 | 100 | 100 | 96 | 99 | 100 | 100 |
|   | 7 | 101 | 100 | 100 | 99 | 99 | 98 |
|   | 14 | 97 | 99 | 98 | 98 | 99 | 98 |
|   | 21 | 100 | 99 | 99 | 100 | 100 | 100 |
| 55 | 0 | 100 | 100 | 100 | 100 | 100 | 100 |
|   | 1 | 100 | 100 | 99 | 99 | 101 | 101 |
|   | 3 | 101 | 103 | 99 | 100 | 100 | 101 |
|   | 7 | 99 | 100 | 99 | 99 | 99 | 100 |
|   | 14 | 96 | 99 | 98 | 99 | 98 | 99 |
|   | 21 | 98 | 99 | 100 | 100 | 100 | 101 |
| 75 | 0 | 100 | 100 | 100 | 100 | 100 | 100 |
|   | 1 | 100 | 100 | 100 | 100 | 100 | 100 |
|   | 3 | 98 | 100 | 100 | 103 | 99 | 99 |
|   | 7 | 95 | 99 | 96 | 99 | 98 | 98 |
|   | 14 | 89 | 98 | 58 | 98 | 95 | 96 |
|   | 21 | 87 | 97 | 15 | 98 | 97 | 42 |

ND = not done;
— = undetermined

TABLE 3

Proportion of impurities (travoprost breakdown products) measured by HPLC analysis.

| Temp. (°C.) | Time (days) | F1 impurities % area | F1 RRT | F2 impurities % area | F2 RRT | F3 impurities % area | F3 RRT | F4 impurities % area | F4 RRT | F5 impurities % area | F5 RRT | F6 impurities % area | F6 RRT |
|---|---|---|---|---|---|---|---|---|---|---|---|---|---|
| 5 | 7 | 0.42 | 0.96 | 0.0 | — | 0.0 | — | 0.0 | — | 1.26 | 0.73 | 1.51 | 0.73 |
|   |   |   |   |   |   |   |   |   |   |   |   | 0.42 | 0.79 |
|   | 14 | ND | ND | ND | ND | ND | ND | ND | ND | ND | ND | ND | ND |
|   | 21 | ND | ND | ND | ND | ND | ND | ND | ND | ND | ND | ND | ND |
| 25 | 7 | 0.77 | 0.96 | 0.0 | — | 0.0 | — | 0.0 | — | 1.38 | 0.73 | 1.51 | 0.73 |
|   |   |   |   |   |   |   |   |   |   |   |   | 0.24 | 0.89 |
|   | 14 | ND | ND | ND | ND | ND | ND | ND | ND | ND | ND | ND | ND |
|   | 21 | ND | ND | ND | ND | ND | ND | ND | ND | ND | ND | ND | ND |
| 40 | 7 | 0.81 | 0.96 | 0.17 | 0.95 | 0.0 | — | 0.0 | — | 1.35 | 0.73 | 1.36 | 0.73 |
|   |   |   |   |   |   |   |   |   |   |   |   | 0.38 | 0.89 |
|   | 14 | 0.0 | — | 0.0 | — | 0.19 | 0.8 | 0.22 | 0.8 | 1.29 | 0.75 | 1.42 | 0.74 |
|   |   |   |   |   |   |   |   |   |   | 0.18 | 0.9 | 0.21 | 0.9 |
|   | 21 | 1.35 | 0.26 | 1.88 | 0.25 | 1.43 | 0.25 | 0.0 | — | 0.36 | 0.94 | 1.28 | 0.77 |
|   |   | 0.63 | 0.94 | 0.13 | 0.96 |   |   |   |   |   |   | 0.47 | 0.94 |
| 55 | 7 | 0.0 | — | 0.51 | 0.97 | 0.0 | — | 0.0 | — | 1.17 | 0.73 | 1.29 | 0.73 |
|   |   |   |   |   |   |   |   |   |   |   |   | 0.2 | 0.89 |
|   | 14 | 0.4 | 0.32 | 0.0 | — | 0.22 | 0.81 | 0.28 | 0.81 | 0.07 | 0.31 | 1.16 | 0.74 |
|   |   |   |   |   |   |   |   |   |   | 1.22 | 0.74 | 0.27 | 0.91 |
|   |   |   |   |   |   |   |   |   |   | 0.35 | 0.91 |   |   |
|   | 21 | 2.33 | 0.32 | 0.21 | 0.96 | 0.0 | — | 0.0 | — | 0.55 | 0.94 | 1.28 | 0.77 |
|   |   | 1.2 | 0.92 |   |   |   |   |   |   |   |   | 0.55 | 0.94 |
| 75 | 7 | 3.18 | 0.32 | 0.94 | 0.31 | 0.57 | 0.31 | 0.0 | — | 0.66 | 0.31 | 0.71 | 0.31 |
|   |   | 0.24 | 0.92 | 0.24 | 0.93 |   |   |   |   | 0.76 | 0.72 | 1.02 | 0.73 |
|   |   |   |   |   |   |   |   |   |   | 0.35 | 0.89 | 0.55 | 0.89 |
|   | 14 | 5.62 | 0.32 | 0.72 | 0.31 | 0.58 | 0.19 | 0.78 | 0.31 | 1.01 | 0.31 | 1.11 | 0.31 |
|   |   |   |   |   |   | 4.47 | 0.25 | 0.2 | 0.8 | 0.47 | 0.75 | 0.47 | 0.74 |
|   |   |   |   |   |   | 1.16 | 0.32 |   |   | 0.56 | 0.91 | 0.51 | 0.91 |
|   |   |   |   |   |   | 1.43 | 0.38 |   |   |   |   |   |   |
|   |   |   |   |   |   | 1.60 | 0.42 |   |   |   |   |   |   |
|   |   |   |   |   |   | 0.54 | 0.51 |   |   |   |   |   |   |
|   |   |   |   |   |   | 0.29 | 0.61 |   |   |   |   |   |   |
|   |   |   |   |   |   | 0.34 | 0.73 |   |   |   |   |   |   |
|   |   |   |   |   |   | 0.23 | 0.86 |   |   |   |   |   |   |
|   |   |   |   |   |   | 4.77 | 0.93 |   |   |   |   |   |   |
|   |   |   |   |   |   | 2.21 | 0.96 |   |   |   |   |   |   |
|   | 21 | 11.9 | 0.32 | 1.67 | 0.32 | 3.67 | 0.17 | 0.19 | 0.26 | 1.96 | 0.32 | 0.48 | 0.10 |
|   |   | 1.08 | 0.93 | 0.12 | 0.96 | 42.01 | 0.26 | 1.82 | 0.32 | 0.89 | 0.94 | 2.62 | 0.17 |
|   |   |   |   |   |   | 3.5 | 0.32 |   |   |   |   | 15.43 | 0.26 |
|   |   |   |   |   |   | 5.8 | 0.38 |   |   |   |   | 2.53 | 0.32 |
|   |   |   |   |   |   | 3.83 | 0.42 |   |   |   |   | 2.25 | 0.38 |
|   |   |   |   |   |   | 3.85 | 0.94 |   |   |   |   | 2.41 | 0.42 |
|   |   |   |   |   |   |   |   |   |   |   |   | 0.79 | 0.94 |

ND = not done;
% area = percent area of each chromatogram;
RRT = relative retention time to main peak (RRT of primary degradant is 0.31).

Example 2

Compositions F2, F4, F5 and F6 of Example 1 were selected for more further analysis at the 40° C. and 55° C. incubation temperatures. At each time point (0, 7, 14, 21, 32, 49, 61 and 100 days) samples were taken for analysis as in Example 1. Thus, the relative potency/activity of each travoprost composition was measured and the proportion of impurities resulting from breakdown products of travoprost was assayed by HPLC analysis. The results of these studies are shown in Table 4. Tables 5 to 8 give a more detailed overview of the results of the HPLC analysis for compositions F2, F4, F5 and F6, respectively.

The results show that the composition containing polysorbate 80 (F2) is as chemically stable as the compositions what contain polyethoxylated castor oil as the surfactant (F4, F5 and F6). Thus, it is clearly demonstrated that polysorbates can be effective in stabilising a prostaglandin in a composition such as an ophthalmic formulation.

TABLE 4

Relative potency (activity) of travoprost and proportion of total detectable impurities.

| Temp. (°C.) | Time (days) | F2 % potency | F2 % impurities | F4 % potency | F4 % impurities | F5 % potency | F5 % impurities | F6 % potency | F6 % impurities |
|---|---|---|---|---|---|---|---|---|---|
| 40 | 0 | 100 | 0.0 | 100 | 0.0 | 100 | 0.0 | 100 | 0.0 |
|   | 7 | 100 | 0.17 | 99 | 0.0 | 99 | 1.35 | 98 | 1.74 |
|   | 14 | 99 | 0.0 | 98 | 0.22 | 99 | 1.47 | 98 | 1.63 |
|   | 21 | 99 | 2.01 | 100 | 0.0 | 100 | 0.36 | 100 | 1.75 |

TABLE 4-continued

Relative potency (activity) of travoprost and proportion of total detectable impurities.

| Temp. (° C.) | Time (days) | F2 % potency | F2 % impurities | F4 % potency | F4 % impurities | F5 % potency | F5 % impurities | F6 % potency | F6 % impurities |
|---|---|---|---|---|---|---|---|---|---|
|  | 32 | 99 | 0.0 | 99 | 0.18 | 99 | 2.85 | 98 | 1.92 |
|  | 49 | 99 | 0.0 | 98 | 0.0 | 99 | 1.47 | 98 | 1.21 |
|  | 61 | 100 | 0.49 | 98 | 4.47 | 99 | 1.7 | 98 | 1.81 |
|  | 100 | 101 | 0.22 | 101 | 0.17 | 101 | 3.26 | 107 | 2.25 |
| 55 | 0 | 100 | 0.0 | 100 | 0.0 | 100 | 0.0 | 100 | 0.0 |
|  | 7 | 100 | 0.51 | 99 | 0.0 | 99 | 1.17 | 100 | 1.49 |
|  | 14 | 99 | 0.0 | 99 | 0.28 | 98 | 1.64 | 99 | 1.43 |
|  | 21 | 99 | 0.21 | 100 | 0.0 | 100 | 0.55 | 101 | 1.83 |
|  | 32 | 100 | 0.0 | 100 | 0.0 | 99 | 1.21 | 99 | 1.59 |
|  | 49 | 98 | 1.51 | 99 | 0.65 | 100 | 1.62 | 99 | 1.82 |
|  | 61 | 99 | 2.47 | 98 | 4.87 | 98 | 2.3 | 98 | 2.46 |
|  | 100 | 100 | 1.36 | 100 | 1.48 | 98 | 2.86 | 8 | 10.48 |

% potency is measured relative to the potency at time zero (0);
% impurities are measured as a percentage of the area under each chromatogram.

TABLE 5

Proportion of impurities detected in composition F2 (travoprost breakdown products) measured by HPLC analysis.

| Time (days) | Temp. (° C.) | % area | RRT | Total % area |
|---|---|---|---|---|
| 7 | 40 | 0.17 | 0.95 | 0.17 |
|  | 55 | 0.51 | 0.97 | 0.51 |
|  | 75 | 0.94 | 0.31 | 1.18 |
|  |  | 0.24 | 0.93 |  |
| 14 | 75 | 0.72 | 0.31 | 0.72 |
| 21 | 40 | 1.88 | 0.25 | 2.01 |
|  |  | 0.13 | 0.96 |  |
|  | 55 | 0.21 | 0.96 | 0.21 |
|  | 75 | 1.67 | 0.12 | 1.79 |
|  |  | 0.12 | 0.96 |  |
| 32 | 75 | 0.66 | 0.27 | 1.69 |
|  |  | 1.03 | 0.32 |  |
| 49 | 55 | 0.41 | 0.32 | 1.51 |
|  |  | 1.1 | 0.96 |  |
|  | 75 | 5.05 | 0.32 | 6.92 |
|  |  | 1.87 | 0.95 |  |
| 61 | 40 | 0.16 | 0.81 | 0.49 |
|  |  | 0.33 | 0.96 |  |
|  | 55 | 0.93 | 0.32 | 2.47 |
|  |  | 1.54 | 0.95 |  |
|  | 75 | 6.74 | 0.32 | 7.75 |
|  |  | 1.01 | 0.95 |  |
| 100 | 40 | 0.17 | 0.80 | 0.22 |
|  |  | 0.05 | 0.94 |  |
|  | 55 | 1.09 | 0.31 | 1.36 |
|  |  | 0.23 | 0.80 |  |
|  |  | 0.04 | 0.95 |  |

RRT = relative retention time to the main peak (RRT of primary degradant free acid is 0.31).

TABLE 6

Proportion of impurities detected in composition F4 (travoprost breakdown products) measured by HPLC analysis.

| Time (days) | Temp. (° C.) | % area | RRT | Total % area |
|---|---|---|---|---|
| 14 | 40 | 0.22 | 0.80 | 0.22 |
|  | 55 | 0.28 | 0.81 | 0.28 |
|  | 75 | 0.78 | 0.31 | 0.98 |
|  |  | 0.20 | 0.80 |  |
| 21 | 75 | 0.18 | 0.26 | 2.00 |
|  |  | 1.82 | 0.32 |  |
| 32 | 40 | 0.18 | 0.81 | 0.18 |
|  | 75 | 1.85 | 0.32 | 2.19 |
|  |  | 0.34 | 0.81 |  |
| 49 | 55 | 0.65 | 0.32 | 0.65 |
|  | 75 | 5.25 | 0.32 | 5.25 |
| 61 | 40 | 4.35 | 0.14 | 4.47 |
|  |  | 0.12 | 0.80 |  |
|  | 55 | 4.33 | 0.14 | 4.87 |
|  |  | 0.42 | 0.32 |  |
|  |  | 0.12 | 0.80 |  |
|  | 75 | 3.81 | 0.14 | 10.89 |
|  |  | 7.08 | 0.31 |  |
| 100 | 40 | 0.17 | 0.81 | 0.17 |
|  | 55 | 1.13 | 0.32 | 1.48 |
|  |  | 0.35 | 0.81 |  |

RRT = relative retention time to the main peak (RRT of primary degradant free acid is 0.31).

TABLE 7

Proportion of impurities detected in composition F5 (travoprost breakdown products) measured by HPLC analysis.

| Time (days) | Temp. (° C.) | % area | RRT | Total % area |
|---|---|---|---|---|
| 7 | 40 | 1.35 | 0.73 | 1.35 |
|  | 55 | 1.17 | 0.73 | 1.17 |
|  | 75 | 0.66 | 0.31 | 1.77 |
|  |  | 0.76 | 0.72 |  |
|  |  | 0.35 | 0.89 |  |
| 14 | 40 | 1.29 | 0.75 | 1.47 |
|  |  | 0.18 | 0.90 |  |
|  | 55 | 0.07 | 0.31 | 1.64 |
|  |  | 1.22 | 0.74 |  |
|  |  | 0.35 | 0.91 |  |
|  | 75 | 1.01 | 0.31 | 2.04 |
|  |  | 0.47 | 0.75 |  |
|  |  | 0.56 | 0.91 |  |
| 21 | 40 | 0.36 | 0.94 | 0.36 |
|  | 55 | 0.55 | 0.94 | 0.55 |
|  | 75 | 1.96 | 0.32 | 2.85 |
|  |  | 0.89 | 0.94 |  |
| 32 | 40 | 1.41 | 0.26 | 2.85 |
|  |  | 1.16 | 0.78 |  |
|  |  | 0.28 | 0.96 |  |
|  | 55 | 1.21 | 0.79 | 1.21 |
|  | 75 | 0.86 | 0.28 | 3.96 |
|  |  | 3.1 | 0.32 |  |

TABLE 7-continued

Proportion of impurities detected in composition F5 (travoprost breakdown products) measured by HPLC analysis.

| Time (days) | Temp. (° C.) | % area | RRT | Total % area |
|---|---|---|---|---|
| 49 | 40 | 1.2 | 0.72 | 1.47 |
|  |  | 0.27 | 0.90 |  |
|  | 55 | 0.44 | 0.32 | 1.62 |
|  |  | 0.88 | 0.72 |  |
|  |  | 0.3 | 0.90 |  |
|  | 75 | 5.5 | 0.31 | 6.43 |
|  |  | 0.37 | 0.50 |  |
|  |  | 0.56 | 0.90 |  |
| 61 | 40 | 1.41 | 0.74 | 1.70 |
|  |  | 0.29 | 0.92 |  |
|  | 55 | 0.79 | 0.32 | 2.30 |
|  |  | 0.87 | 0.74 |  |
|  |  | 0.64 | 0.92 |  |
|  | 75 | 0.23 | 0.28 | 8.68 |
|  |  | 7.78 | 0.32 |  |
|  |  | 0.2 | 0.85 |  |
|  |  | 0.47 | 0.92 |  |
| 100 | 40 | 1.09 | 0.24 | 3.26 |
|  |  | 1.86 | 0.74 |  |
|  |  | 0.31 | 0.92 |  |
|  | 55 | 1.37 | 0.31 | 2.86 |
|  |  | 0.80 | 0.73 |  |
|  |  | 0.69 | 0.91 |  |

RRT = relative retention time to the main peak (RRT of primary degradant free acid is 0.31).

TABLE 8

Proportion of impurities detected in composition F6 (travoprost breakdown products) measured by HPLC analysis.

| Time (days) | Temp. (° C.) | % area | RRT | Total % area |
|---|---|---|---|---|
| 7 | 40 | 1.36 | 0.73 | 1.74 |
|  |  | 0.38 | 0.89 |  |
|  | 55 | 1.29 | 0.73 | 1.49 |
|  |  | 0.20 | 0.89 |  |
|  | 75 | 0.71 | 0.31 | 2.28 |
|  |  | 1.02 | 0.73 |  |
|  |  | 0.55 | 0.89 |  |
| 14 | 40 | 1.42 | 0.74 | 1.63 |
|  |  | 0.21 | 0.90 |  |
|  | 55 | 1.16 | 0.74 | 1.43 |
|  |  | 0.27 | 0.91 |  |
|  | 75 | 1.11 | 0.31 | 2.09 |
|  |  | 0.47 | 0.74 |  |
|  |  | 0.51 | 0.91 |  |
| 21 | 40 | 1.28 | 0.77 | 1.75 |
|  |  | 0.47 | 0.94 |  |
|  | 55 | 1.28 | 0.77 | 1.83 |
|  |  | 0.55 | 0.94 |  |
|  | 75 | 0.48 | 0.10 | 26.51 |
|  |  | 2.62 | 0.17 |  |
|  |  | 15.43 | 0.26 |  |
|  |  | 2.53 | 0.32 |  |
|  |  | 2.25 | 0.38 |  |
|  |  | 2.41 | 0.42 |  |
| 32 | 40 | 1.53 | 0.78 | 1.92 |
|  |  | 0.39 | 0.95 |  |
|  | 55 | 1.25 | 0.78 | 1.59 |
|  |  | 0.34 | 0.95 |  |
|  | 75 | 0.49 | 0.28 | 4.16 |
|  |  | 3.18 | 0.32 |  |
|  |  | 0.49 | 0.95 |  |
| 49 | 40 | 1.21 | 0.72 | 1.21 |
|  | 55 | 0.57 | 0.31 | 1.82 |
|  |  | 0.46 | 0.50 |  |
|  |  | 0.79 | 0.72 |  |
|  | 75 | 0.18 | 0.27 | 6.46 |
|  |  | 5.86 | 0.31 |  |
|  |  | 0.25 | 0.50 |  |
|  |  | 0.17 | 0.73 |  |
| 61 | 40 | 1.42 | 0.73 | 1.81 |
|  |  | 0.39 | 0.90 |  |
|  | 55 | 0.79 | 0.31 | 2.46 |
|  |  | 0.91 | 0.73 |  |
|  |  | 0.76 | 0.90 |  |
|  | 75 | 7.84 | 0.31 | 8.50 |
|  |  | 0.38 | 0.83 |  |
|  |  | 0.28 | 0.90 |  |
| 100 | 40 | 1.83 | 0.73 | 2.25 |
|  |  | 0.42 | 0.90 |  |
|  | 55 | 7.07 | 0.37 | 10.48 |
|  |  | 3.41 | 0.92 |  |

RRT = relative retention time to the main peak (RRT of primary degradant free acid is 0.31).

The invention claimed is:

1. A pharmaceutical composition comprising:

| travoprost | 0.002-0.008% w/v |
| polysorbate 80 | 0.4-0.6% w/v |
| benzalkonium chloride | 0.010-0.020% w/v |
| EDTA | 0.05-0.2% w/v |
| boric acid | 0.1-0.4% w/v |
| tromethamine | 0.08-0.2% w/v |
| mannitol | 2.0-8.0% w/v. |

2. A pharmaceutical composition according to claim 1, comprising:

| travoprost | 0.004% w/v |
| polysorbate 80 | 0.5% w/v |
| benzalkonium chloride | 0.015% w/v |
| EDTA | 0.1% w/v |
| boric acid | 0.3% w/v |
| tromethamine | 0.12% w/v |
| mannitol | 4.6% w/v. |

3. A pharmaceutical composition of claim 1, wherein the composition has a pH in the range 5.0 to 7.5.

4. A pharmaceutical composition of claim 3, wherein the pH is approximately 6.0.

5. A pharmaceutical composition according to claim 1 for topical applications.

6. A pharmaceutical composition according to claim 5 for use in the treatment of ocular hypertension.

7. A pharmaceutical composition according to claim 5 for use in the treatment of glaucoma.

* * * * *

UNITED STATES PATENT AND TRADEMARK OFFICE
CERTIFICATE OF CORRECTION

| | | |
|---|---|---|
| PATENT NO. | : 8,084,501 B2 | Page 1 of 1 |
| APPLICATION NO. | : 11/336115 | |
| DATED | : December 27, 2011 | |
| INVENTOR(S) | : Victor Deaciuc et al. | |

It is certified that error appears in the above-identified patent and that said Letters Patent is hereby corrected as shown below:

Title Page

Under (73) Assignees: Please delete "Resolution Chemicals Limited, Hertfordshire (GB)"

Signed and Sealed this
Twenty-sixth Day of February, 2013

Teresa Stanek Rea
*Acting Director of the United States Patent and Trademark Office*